United States Patent
De Coninck

(10) Patent No.: US 7,704,270 B2
(45) Date of Patent: Apr. 27, 2010

(54) VARIABLE OFFSET CONNECTORS AND BONE FIXATION METHODS

(75) Inventor: Cédric De Coninck, Cestas Gazinet (FR)

(73) Assignee: Stryker Spine (FR)

(*) Notice: Subject to any disclaimer, the term of this patent is extended or adjusted under 35 U.S.C. 154(b) by 1342 days.

(21) Appl. No.: 11/019,824

(22) Filed: Dec. 22, 2004

(65) Prior Publication Data

US 2006/0149234 A1 Jul. 6, 2006

(51) Int. Cl.
A61B 17/70 (2006.01)
A61F 2/08 (2006.01)
A61B 17/86 (2006.01)

(52) U.S. Cl. .................. 606/264; 606/278; 606/301

(58) Field of Classification Search ............ 606/61, 606/250–253, 260, 264, 278, 301, 305, 306; 623/17.11–17.16; 6/61
See application file for complete search history.

(56) References Cited

U.S. PATENT DOCUMENTS

| | | | |
|---|---|---|---|
| 5,002,578 A | 3/1991 | Luman | |
| 5,261,909 A | 11/1993 | Sutterlin et al. | |
| 5,312,404 A * | 5/1994 | Asher et al. | 606/264 |
| 5,653,765 A | 8/1997 | McTighe et al. | |
| 5,702,480 A | 12/1997 | Kropf et al. | |
| 5,741,255 A * | 4/1998 | Krag et al. | 606/61 |
| 5,976,135 A * | 11/1999 | Sherman et al. | 606/278 |
| 5,984,924 A * | 11/1999 | Asher et al. | 606/264 |
| 6,146,383 A * | 11/2000 | Studer et al. | 606/308 |
| 6,187,005 B1 * | 2/2001 | Brace et al. | 606/264 |
| 6,231,575 B1 | 5/2001 | Krag | |
| 6,309,390 B1 * | 10/2001 | Le Couedic et al. | 606/264 |
| 6,478,798 B1 | 11/2002 | Howland | |
| 6,520,962 B1 | 2/2003 | Taylor et al. | |
| 6,641,583 B2 | 11/2003 | Shluzas et al. | |
| 6,682,529 B2 * | 1/2004 | Stahurski | 606/301 |
| 7,306,602 B2 * | 12/2007 | Bono et al. | 606/292 |
| 2002/0040244 A1 | 4/2002 | Despres, III et al. | |
| 2002/0143328 A1 | 10/2002 | Shluzas et al. | |
| 2002/0173789 A1 | 11/2002 | Howland | |
| 2002/0173791 A1 | 11/2002 | Howland | |
| 2003/0045878 A1 * | 3/2003 | Petit et al. | 606/61 |
| 2003/0045879 A1 | 3/2003 | Minfelde et al. | |
| 2003/0153913 A1 | 8/2003 | Altarac et al. | |
| 2003/0163133 A1 | 8/2003 | Altarac et al. | |
| 2004/0087949 A1 * | 5/2004 | Bono et al. | 606/61 |
| 2005/0070901 A1 * | 3/2005 | David | 606/61 |

(Continued)

FOREIGN PATENT DOCUMENTS

CA 2393150 6/2001

(Continued)

OTHER PUBLICATIONS

European Search Report, EP 05 29 2771, Dated Mar. 28, 2006.

*Primary Examiner*—Eduardo C Robert
*Assistant Examiner*—Ellen C Hammond
(74) *Attorney, Agent, or Firm*—Lerner, David, Littenberg, Krumholz & Mentlik, LLP

(57) ABSTRACT

A bone fixation assembly for use in spinal fixation surgery is disclosed. The bone fixation assembly has a rod receiving portion, a sliding component, a first locking element, and a second locking element. A method of fixing two vertebrae with respect to each other is also disclosed.

22 Claims, 8 Drawing Sheets

U.S. PATENT DOCUMENTS

2006/0095037 A1* 5/2006 Jones et al. .................. 606/61
2006/0149231 A1* 7/2006 Bray .......................... 606/61

FOREIGN PATENT DOCUMENTS

| CA | 2447844 | 4/2004 |
| EP | 1 417 935 A | 5/2004 |
| WO | WO-03/068088 A | 8/2003 |

* cited by examiner

VARIABLE OFFSET CONNECTORS AND BONE FIXATION METHODS

BACKGROUND OF THE INVENTION

The spinal column is a highly complex system of bones and connective tissues that provides support for the body and protects the delicate spinal cord and nerves. The spinal column includes a series of stacked vertebral bodies, each vertebral body including an inner or central portion of relatively weak cancellous bone and an outer portion of relatively strong cortical bone. Situated between each vertebral body is an intervertebral disc that cushions and dampens compressive forces exerted upon the spinal column. A vertebral canal containing the spinal cord and nerves is located behind the vertebral bodies.

A surgical technique commonly referred to as spinal fixation uses surgical implants for fusing together and/or mechanically immobilizing two or more vertebral bodies of the spinal column. Spinal fixation may also be used to alter the alignment of adjacent vertebral bodies relative to one another to change the overall alignment of the spinal column. Such techniques have been used effectively to treat a wide variety of conditions and, in most cases, to relieve pain.

One spinal fixation technique involves immobilizing the spine using orthopedic stabilizing rods, commonly referred to as spinal rods, which run generally parallel to the spine. This technique involves exposing the spine posteriorly and fastening bone screws to the pedicles of vertebral bodies. The pedicle screws are generally placed at least one per vertebra and serve as anchor points for the spine rods. Clamping elements adapted for receiving a spine rod therethrough are then used to join the spine rods to the pedicle screws. The aligning influence of the spine rods forces the spinal column to conform to a more desirable shape. In certain instances, the spine rods may be bent to achieve the desired curvature of the spinal column.

Most existing rod fixation systems require several components to build the systems. Each additional component or instrument required to assemble the fixation system adds to the complexity of the surgical technique. Furthermore, such systems rarely fulfill a surgeon's expectations when it comes to adjustability. A need has thus arisen for improved fixation systems that minimize the assembly of small pieces of hardware during the surgical procedure and allow for easy adjustments to be made during surgery. Thus, there remains a need for spinal fixation devices that facilitate simple, fast, and customizable assembly of attachment of a spinal rod to a spine. It would be desirable to provide a device with pre-assembled components that will result in less time in assembling the components in the operating room and allow a surgeon to easily configure such a device to properly fit a patient.

SUMMARY OF THE INVENTION

The invention relates to bone fixation devices, and in particular, to spinal fixation assemblies and methods used to correct spinal deformities or injuries.

A first aspect of the present invention is a bone fixation assembly comprising a rod receiving portion having a first opening for receiving a rod, and an elongate second opening for receiving a portion of a fixation element; a sliding component having a third opening for receiving a portion of the fixation element, and a channel for slidably receiving a portion of the rod receiving portion, the second and third openings being alignable so that the fixation element can be inserted therethrough, the channel allowing movement of the sliding component and the fixation element with respect to the rod receiving portion and the rod disposed in the first opening; a first locking element associated with the rod receiving portion to secure the rod in the first opening; and a second locking element associated with the sliding component to secure the fixation element in the second and third openings.

In some embodiments, the bone fixation assembly further comprises a fixation element having a head portion inserted in the second and third openings. In some embodiments, the second locking element comprises a locking nut and a ball ring which cooperates with the locking nut. In some of these embodiments, the locking nut and ball ring may be permanently seated in the third opening. In other of these embodiments, the locking nut includes a head having multiple prongs and contains external male threads that engage female threads formed in the third opening. The aforementioned engagement of the male threads of the locking nut with the female threads in the third opening exert a radial force on the ball ring to secure a portion of the fixation element in the third opening. When the locking nut is in a locked position, the ball ring is in contact with the sliding component and the locking nut, maintaining the sliding component in a fixed position.

In some additional embodiments, the first locking element is a set screw. This set screw may be permanently seated in the rod receiving portion. In other embodiments, the third opening may have an axis which is substantially transverse to an axis of the first opening.

Another embodiment of the present invention pertains to a variable offset connector comprising a rod receiving portion having a first channel adapted to receive a spinal rod and second channel adapted to receive a portion of a fixation element, the fixation element being able to move in a direction towards and away from the spinal rod; a first locking element associated with the rod receiving portion for selectively preventing movement of the spinal rod; and a second locking element associated with the rod receiving portion for selectively preventing movement of the fixation element. The variable offset connector may further include a fixation element having a portion inserted in the second channel.

A second aspect of the present invention is a method of fixing a vertebra with respect to another vertebra. The method according to an embodiment of the present invention comprises the steps of providing at least two connectors adapted to facilitate connection between a spinal rod and a fixation element, the connectors adapted to allow polyaxial movement and sliding movement of the fixation element with respect to the spinal rod; providing at least two fixation elements having head portions; attaching the fixation elements to different vertebra; inserting the spinal rod through a first bore of each of the connectors; sliding a second bore of each of the connectors over the head portions of the screws; adjusting a position of the spinal rod with respect to the fixation element; tightening a first locking element of each connector associated with the first bore to secure the spinal rod to the connector; and tightening a second locking element of each connector associated with the second bore to secure the head portion of the screw to the connector. In other embodiments, the step of adjusting a position of the spinal rod with respect to the fixation elements includes adjusting the polyaxial and medial-lateral positions. Furthermore, other embodiments include the step of attaching extensions to the fixation elements to facilitate easier sliding of the second bore of each of the connectors over the head portions of the screws.

Another embodiment of the second aspect of the present invention is a method of spinal fixation. The method of this embodiment comprises attaching at least two fixation elements to at least two different vertebrae of a spine; providing at least two variable offset connectors adapted to facilitate connection between a spinal rod and the fixation elements, the connectors adapted to allow polyaxial movement and medial-lateral movement of the fixation element with respect to the spinal rod; attaching a spinal rod to the connectors; adjusting the position of the spinal rod with respect to the fixation elements; and attaching the connectors to the fixation elements.

BRIEF DESCRIPTION OF THE DRAWINGS

A more complete appreciation of the subject matter of the present invention and the various advantages thereof can be realized by reference to the following detailed description in which reference is made to the accompanying drawings in which.

DETAILED DESCRIPTION

Figure 1:
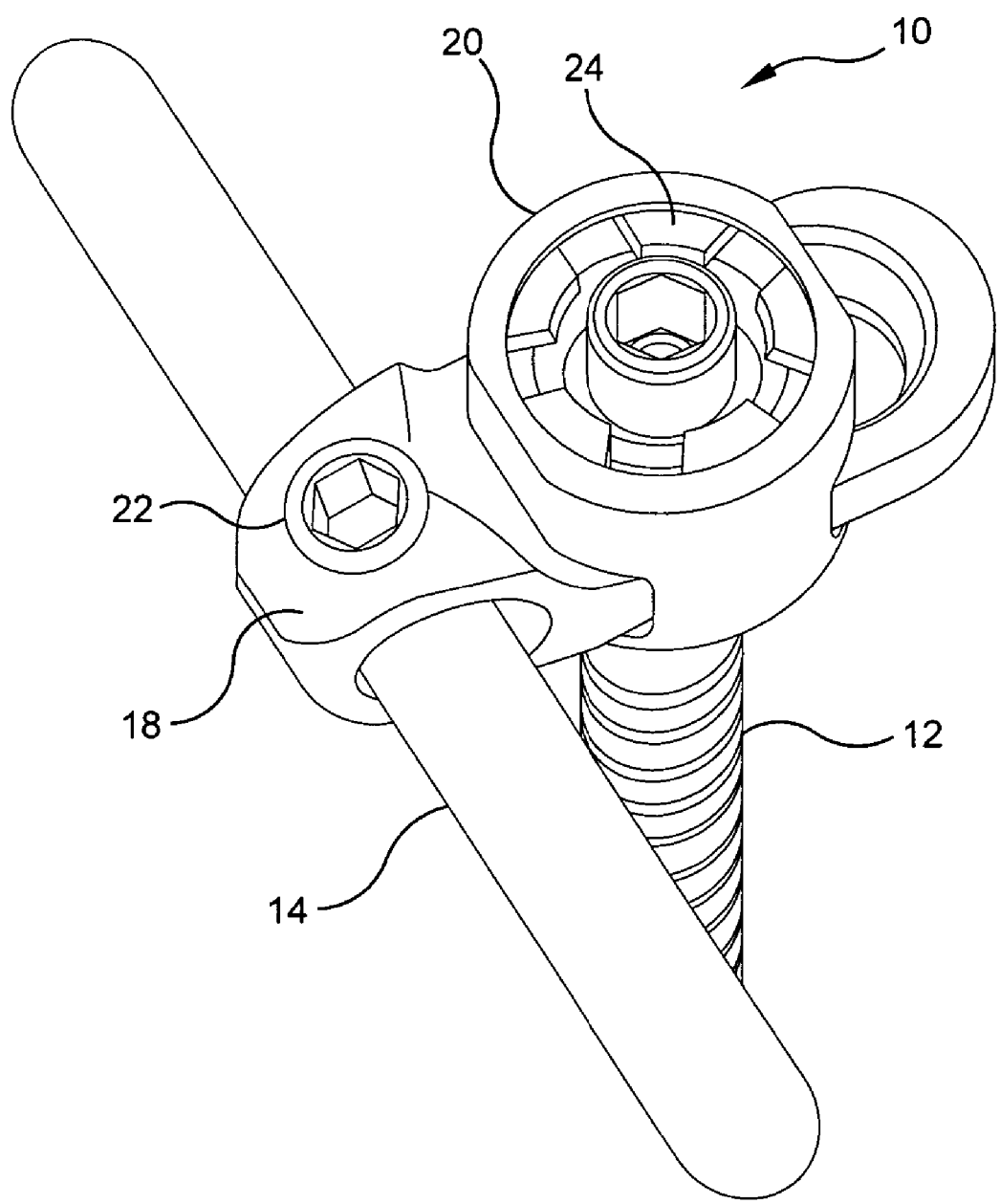
FIG. 1 is a top perspective view of the apparatus according to an embodiment of the present invention.

In describing the preferred embodiments of the subject matter illustrated and to be described with respect to the drawings, specific terminology will be used for the sake of clarity. However, the invention is not intended to be limited to any specific terms used herein, and it is to be understood that each specific term includes all technical equivalents which operate in a similar manner to accomplish a similar purpose.

Referring to the drawings, wherein like reference numerals represent like elements, there is shown in FIGS. 1-11, in accordance with various embodiments of the present invention, a variable offset connector, designated generally by reference numeral 10. The variable offset connector 10 is typically used in conjunction with a fixation element 12, such as a screw or hook, and a spinal rod 14. In a preferred embodiment, fixation element 12 is a polyaxial screw. The variable offset connector 10 may be used in spinal fixation surgery, during which connector 10 may be secured to pedicles of the vertebral bodies of a spinal column. In a preferred embodiment, connector 10 includes a rod receiving portion 18, a sliding component 20, a first locking element, or set screw 22, and a second locking element 24. The various elements of connector 10 are preferably constructed of biologically inert materials, such as metals customarily used for surgical devices like bone screws and pins. This material may be titanium or stainless steel, but could be other suitable materials, for example, alloys, composite materials, ceramics, or carbon fiber materials.

Figure 2:
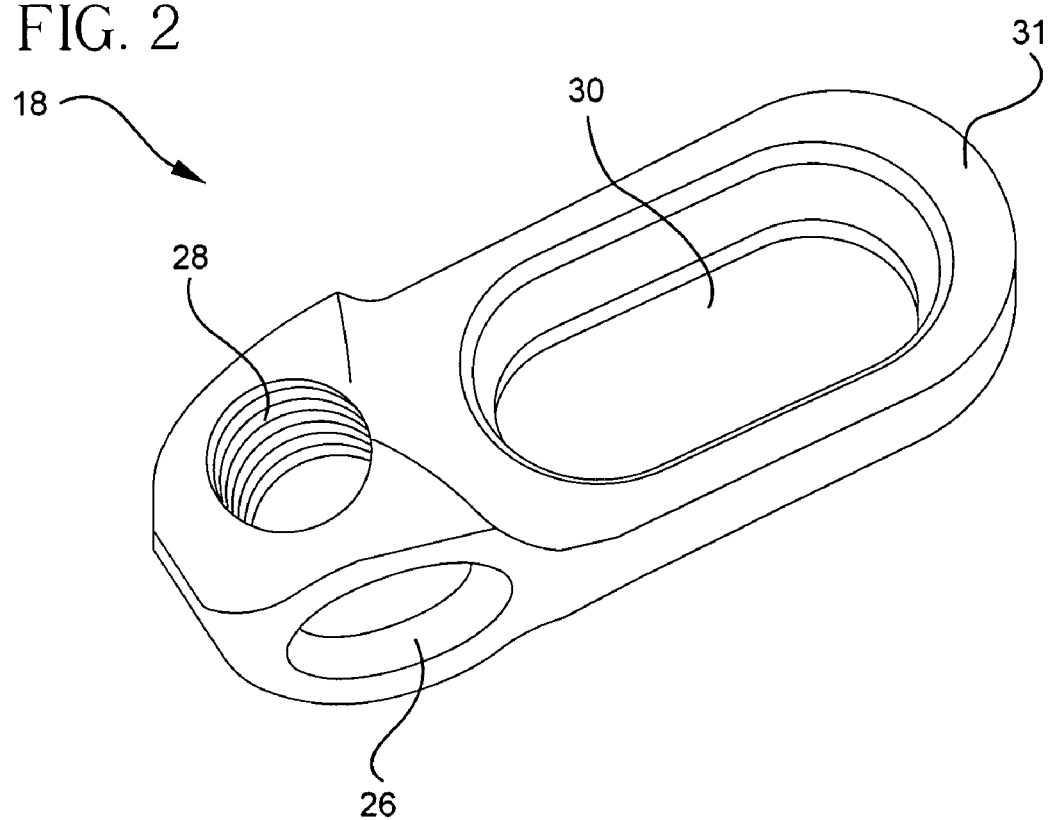
FIG. 2 is a top perspective view of the rod receiving portion according to the embodiment of FIG. 1.

FIG. 2 shows rod receiving portion 18 separated from the other elements of connector 10. As shown in the figure, rod receiving portion 18 includes a first opening 26, a set screw bore 28, and an elongate second opening 30. First opening 26 allows spinal rod 14 to extend therethrough. Essentially, first opening 26 is a void through the body of rod receiving portion 18. However, it is contemplated that first opening 26 could be a channel open on one side. Set screw bore 28 is also a void extending through a portion of rod receiving portion 18. Set screw bore 28 extends through the body of rod receiving portion 18 and into first opening 26. In a preferred embodiment, set screw bore 28 extends in a direction substantially transverse to that of first opening 26 and includes interior threads therein. The exterior threads of set screw 22 (best shown in FIG. 8) mate with interior threads in set screw bore 28. Upon tightening of set screw 22 within set screw bore 28, set screw 22 contacts spinal rod 14. This restricts movement of spinal rod 14 with respect to rod receiving portion 18. Elongate second opening 30 extends along extension 31 of rod receiving portion 18. Second opening 30, in cooperation with sliding component 20, allows for medial-lateral movement of fixation element 12 with respect to spinal rod 14. This will be discussed further below.

Figure 3:
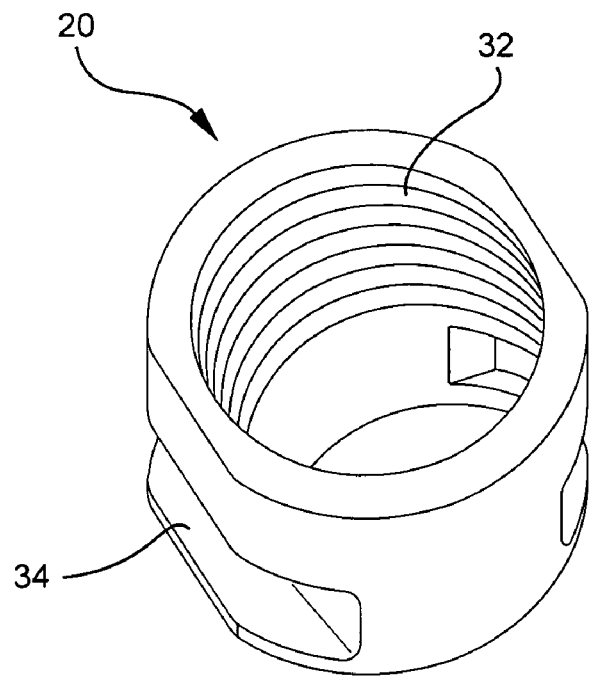
FIG. 3 is a top perspective view of the sliding component according to the embodiment of FIG. 1.
Figure 4:
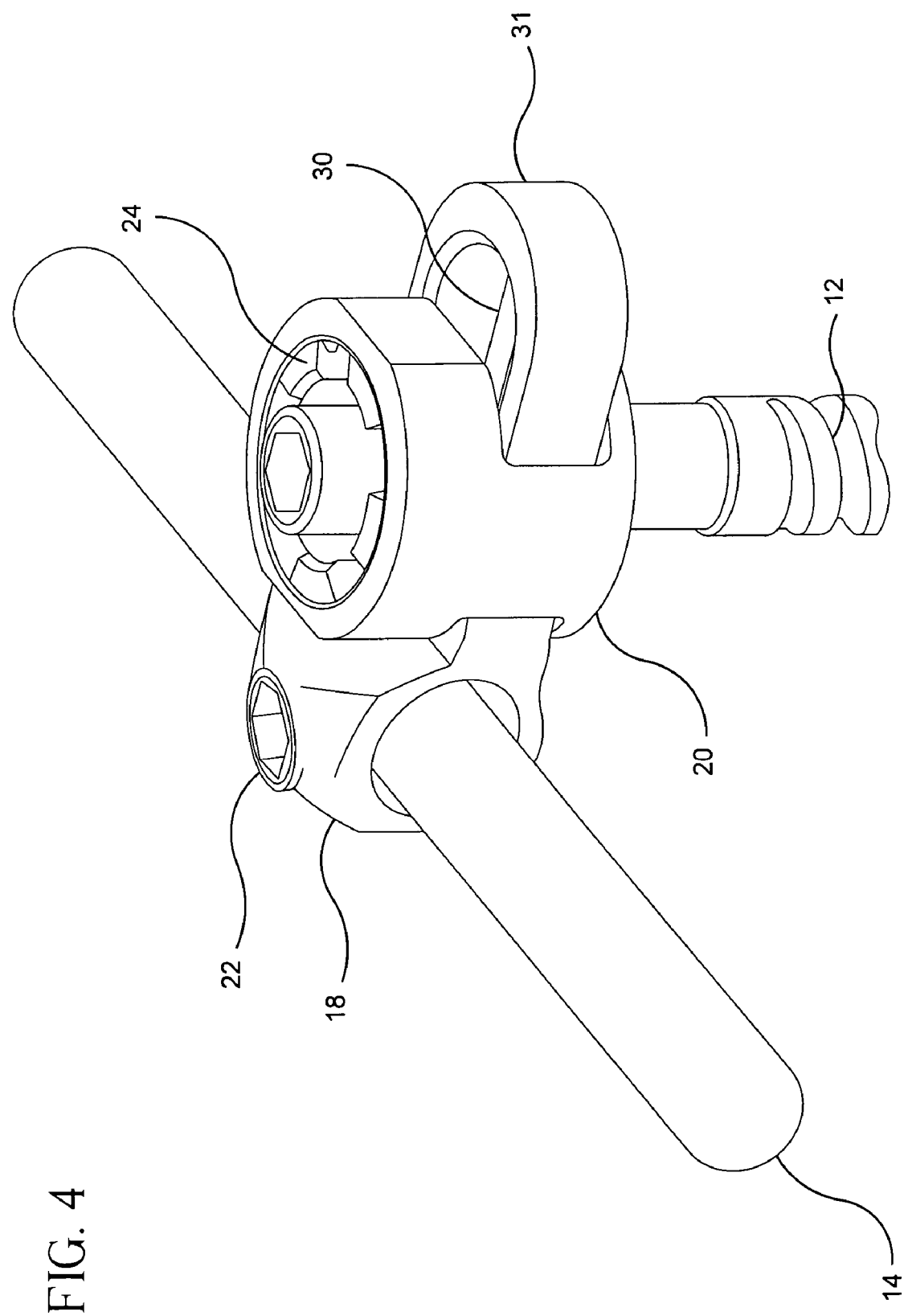
FIG. 4 is a side perspective view of the apparatus according to the embodiment of FIG. 1.
Figure 5:
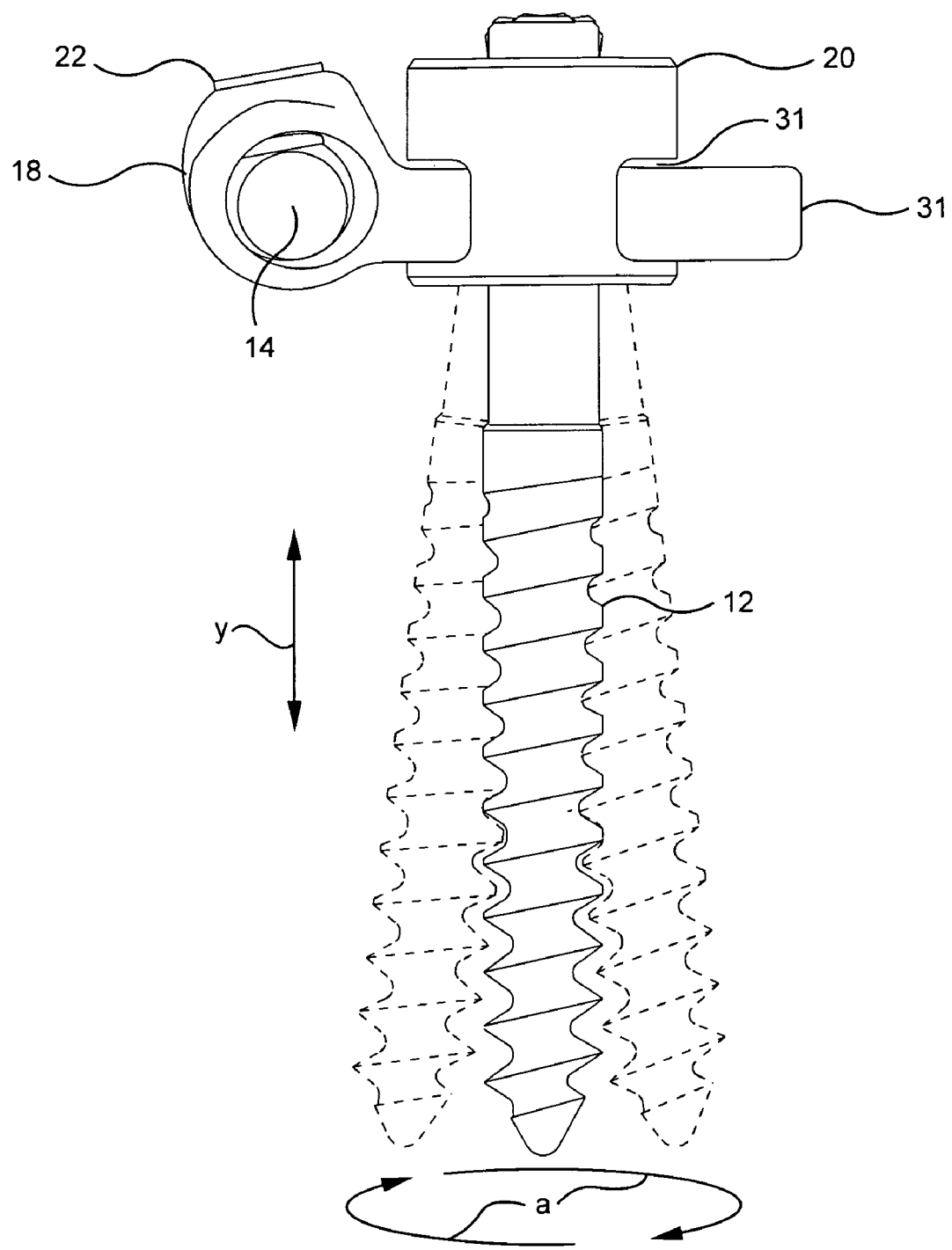
FIG. 5 is a side view of the apparatus according to the embodiment of FIG. 1 showing the polyaxial movement of the fixation element.

FIG. 3 illustrates sliding component 20, separated from rod receiving portion 18. Sliding component 20 includes third opening 32 and channel 34. Third opening 32 is configured to receive fixation element 12 and also serves as a seat for the second locking element 24. As shown in FIGS. 1 and 4, second locking element 24 is utilized to selectively retain fixation element 12. This will be discussed further below. Channel 34 is an elongate opening which extends in a transverse direction to that of third opening 32. In a preferred embodiment, channel 34 intersects third opening 32. Preferably, channel 34 is configured to receive at least a segment of rod receiving portion 18, and allows sliding component 20 to move relative to rod receiving portion 18. In a preferred embodiment, channel 34 is configured to receive extension 31 rod receiving portion 18, which includes second opening 30. This allows third opening 32 to align with second opening 30.

Figure 6:
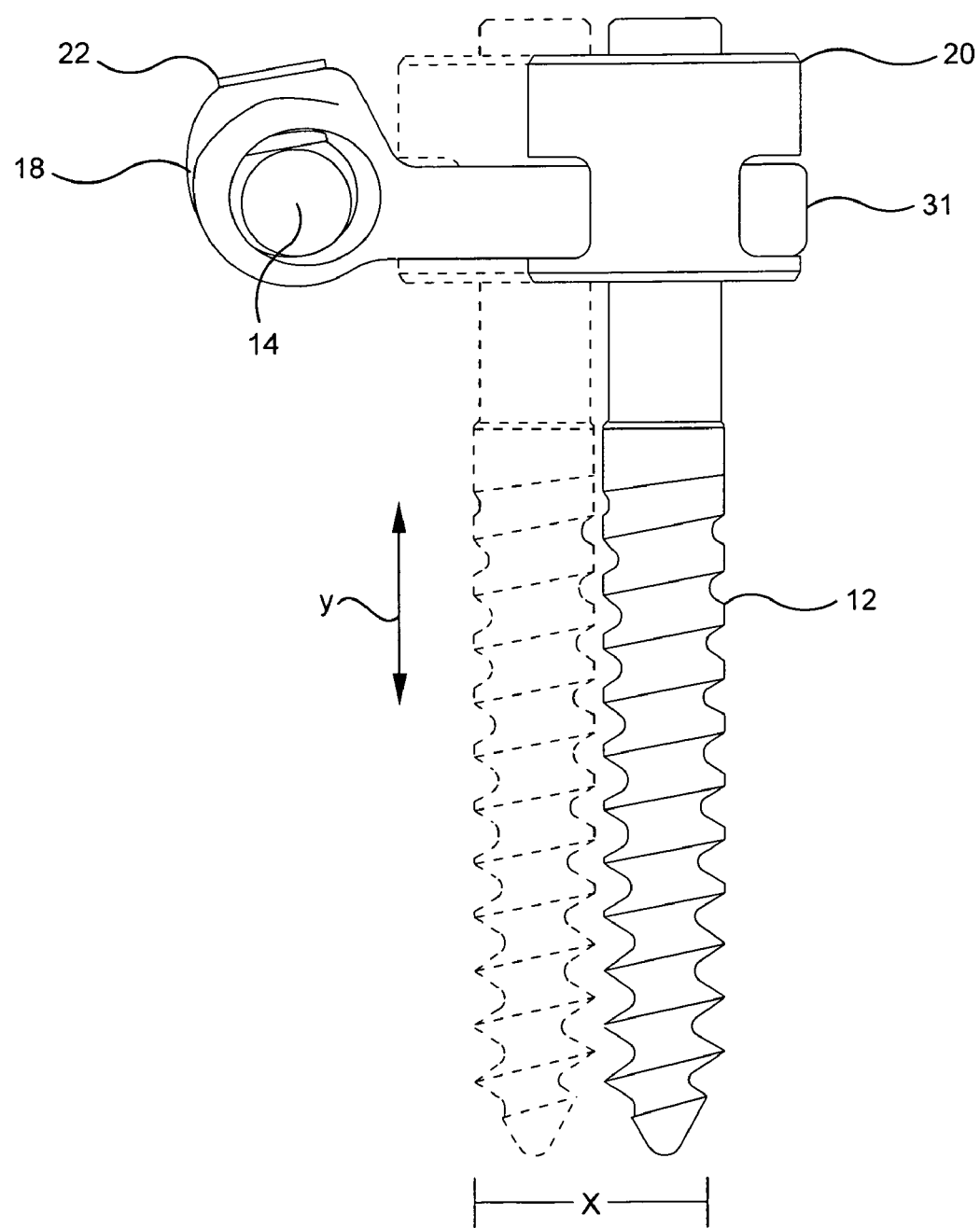
FIG. 6 is a side view of the apparatus according to the embodiment of FIG. 1 showing the medial-lateral movement of the sliding component and fixation element.

A completely constructed form of connector 10 is shown in FIGS. 1 and 4-6. Sliding component 20 is connected with rod receiving portion 18 by inserting extension 31 into channel 34. As mentioned above, this aligns second opening 30 and third opening 32, to form one continuous opening for receiving fixation element 12. Spinal rod 14 is inserted into first opening 26, and set screw 22 is tightened to prevent any movement of spinal rod 14 therein. With fixation element 12 extending through second opening 30 and third opening 32, sliding component 20 and fixation element 12 are capable of being moved in a medial-lateral direction with respect to spinal rod 14 (best shown in FIG. 6). Sliding component 20 and fixation element 12 are essentially able to move in a length substantially equal to a length of second opening 30. As shown in FIG. 6, this distance is represented by a distance x. This movement allows a surgeon to configure connector 10 to properly fit a patient's unique anatomy and size.

Figure 9:
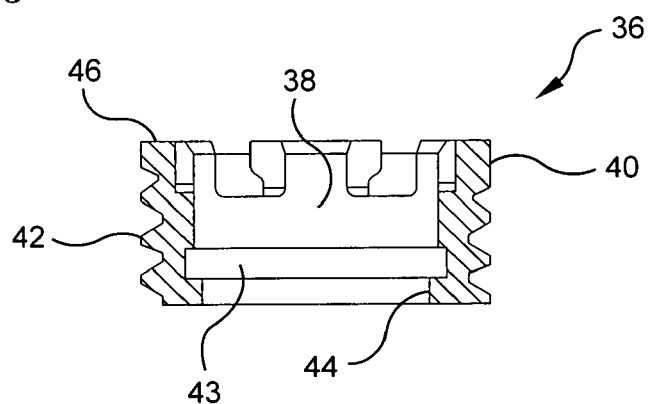
FIG. 9 is a cross sectional view of a portion of the second locking element according to the embodiment of FIG. 1.

In a preferred embodiment, second locking element 24 includes a locking nut 36. Further detail on locking nut 36 is shown in FIG. 9. Preferably, locking nut 36 is hollow and has a bore 38 therethrough for receiving a portion of fixation element 12. The locking nut 36 includes a receiving end 40, where bore 38 at receiving end 40 is flared or angled as shown in FIG. 9. This flared or tapered opening permits polyaxial motion of a fixation element inserted therethrough. Also in a preferred embodiment, third opening 32 includes a bottom portion 33 that is tapered or flared in a direction opposite the taper or flared opening in locking nut 36. The oppositely extended flared openings permit polyaxial movement between fixation element 12 and sliding component 20. This is illustrated by the distance "a" shown in FIG. 5. In preferred embodiments, fixation element 12 can move by at least 20 degrees polyaxially, as shown by distance "a". It is noted that the polyaxial motion of fixation element 12 can occur a distance "a" in all directions three hundred sixty degrees around an axis. Furthermore, fixation element 12 is adjustable in height in an anterior-posterior direct with respect to sliding component 20. This is illustrated by the distance "y" also shown in FIG. 5. Locking nut 36 further includes a seating end 42, and according to at least one embodiment, seating end 42 includes a slot 43 and an inner engagement surface 44 for engaging a ball ring or other element, which will be described in more detail below. The receiving end 40 of locking nut 36 may further include surfaces adapted to receive a wrench or other device adapted to turn locking nut 26. In the preferred embodiment, locking nut 36 includes a plurality of prongs 46, which are capable of being turned by a corresponding tightening instrument 48. This is show in more detail in FIG. 7 and discussed more fully below. Finally, in certain preferred embodiments, the exterior surface of receiving end 40 further includes male threads for engagement with complementary female threads on the interior of third opening 32 of sliding component 20.

Figure 11:
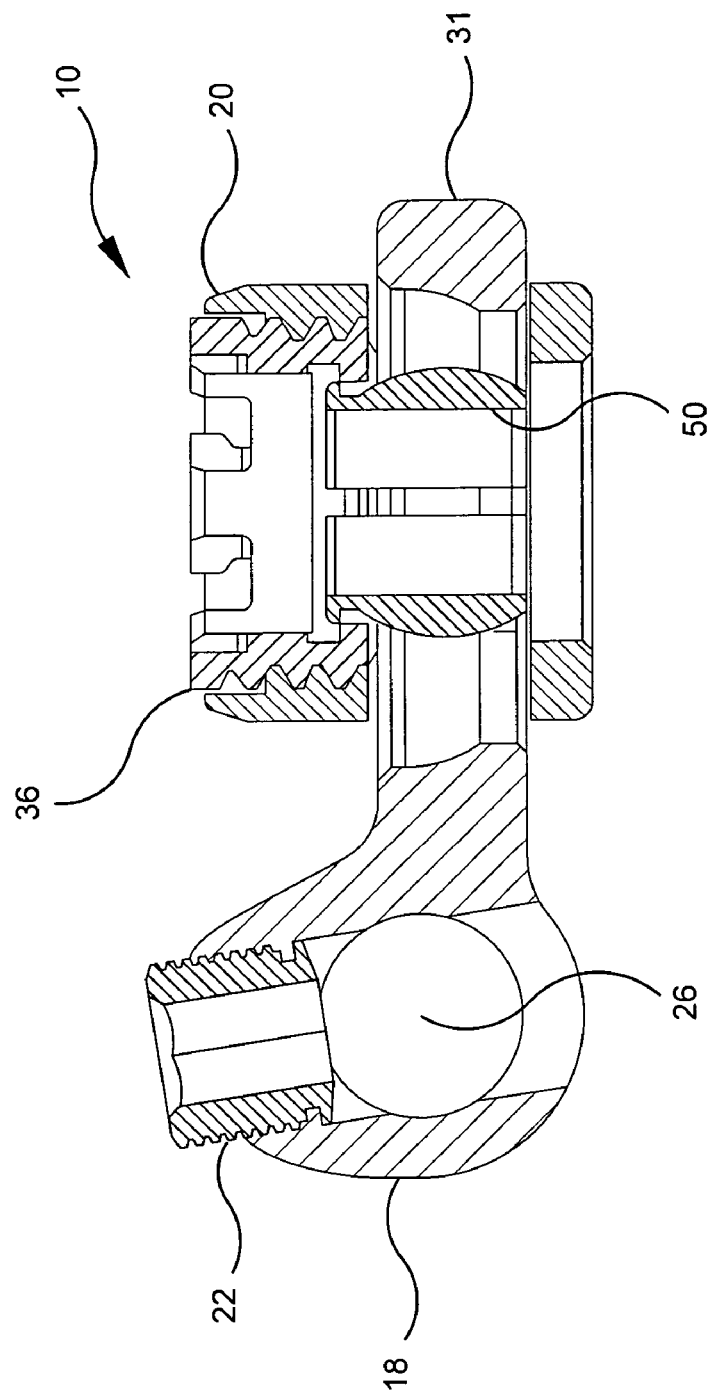
FIG. 11 is a cross-sectional view of the apparatus according to the embodiment of FIG. 1 showing more detail of the first and second locking elements.

According to preferred embodiments of the present invention, the second locking element 24 further includes a ball ring 50 which cooperates with locking nut 36 to lock fixation element 12 to sliding component 20. As best shown in FIG. 11, ball ring 50 is seated within the third opening 32 and at least a portion of locking nut 36 circumferentially surrounds a portion of ball ring 50. In preferred embodiments, ball ring 50 is pre-assembled and permanently seated in third opening 32 of sliding component 20 and inner engagement surface 44 engages groove 53 of ball ring 50.

Figure 10:
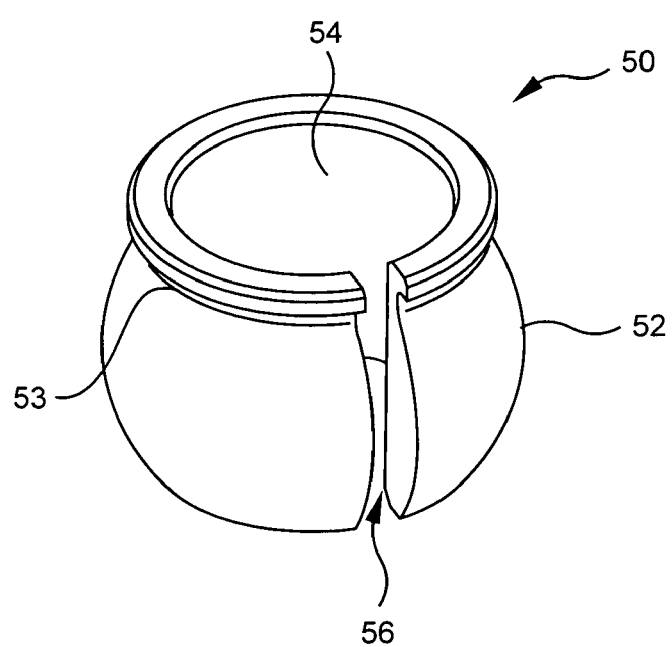
FIG. 10 is a top perspective view of another portion of the second locking element according to the embodiment of FIG. 1.

Ball ring 50, as shown by itself in FIG. 10, comprises a generally spherical outer surface 52 having a ball ring opening 54 through the body coaxial with third opening 32 and adapted to receive a portion of fixation element 12. Ball ring 50 further includes a gap 56 in the outer surface, allowing ball ring 50 to be compressed such that the inner diameter of ball ring 50 is reduced when ball ring 50 is compressed. Ball ring 50 and gap 56 are designed such that when ball ring 50 is compressed, the diameter of ball ring opening 54 is less than the diameter of a portion of fixation element 12. This allows for fixation element 12 to be securely and snugly held in place. Finally, ball ring 50 includes groove 53 for receiving inner engagement surface 44 of locking nut 36. This groove 53 is located on a collar in the upper portion of ball ring 50. When groove 53 is in engagement with inner engagement surface 44, a portion of ball ring 50 extends into slot 43. This allows for ball ring 50 to be seated in locking nut 36 and compression of ball ring 50 occurs when locking nut 36 is tightened. Engagement of the male thread of locking nut 36 with the female threads in third opening 32 cause the inner engagement surface 44 of locking nut 36 to engage groove 53 of ball ring 50, causing ball ring 50 to compress onto a portion of fixation element 12. This compression exerts a radial force on exterior surface 52 of ball ring 50. It is to be understood that ball ring 50 may be configured differently than shown in the Figures. For example, instead of a single gap 56 in exterior surface 52, ball ring 50 may include a plurality of split openings that do not extend through the entire exterior surface of the split ring.

In addition to selectively preventing polyaxial movement of fixation element 12, second locking element 24 is also configured to prevent medial-lateral movement of fixation element 12 and sliding component 20 with respect to spinal rod 14. Upon tightening of locking nut 36 in third opening 32, ball ring 50 will make contact with rod receiving portion 18 (shown best in FIG. 11). Upon sufficient tightening of locking nut 36, enough pressure is exerted on rod receiving portion 18 by ball ring 50 that sliding component 20 may no longer move relative to rod receiving portion 18. Therefore, with the single step of tightening locking nut 36, prevents both polyaxial movement of fixation element 12 and medial-lateral movement of fixation element 12 and sliding component 20 with respect to spinal rod 14.

Figure 7:
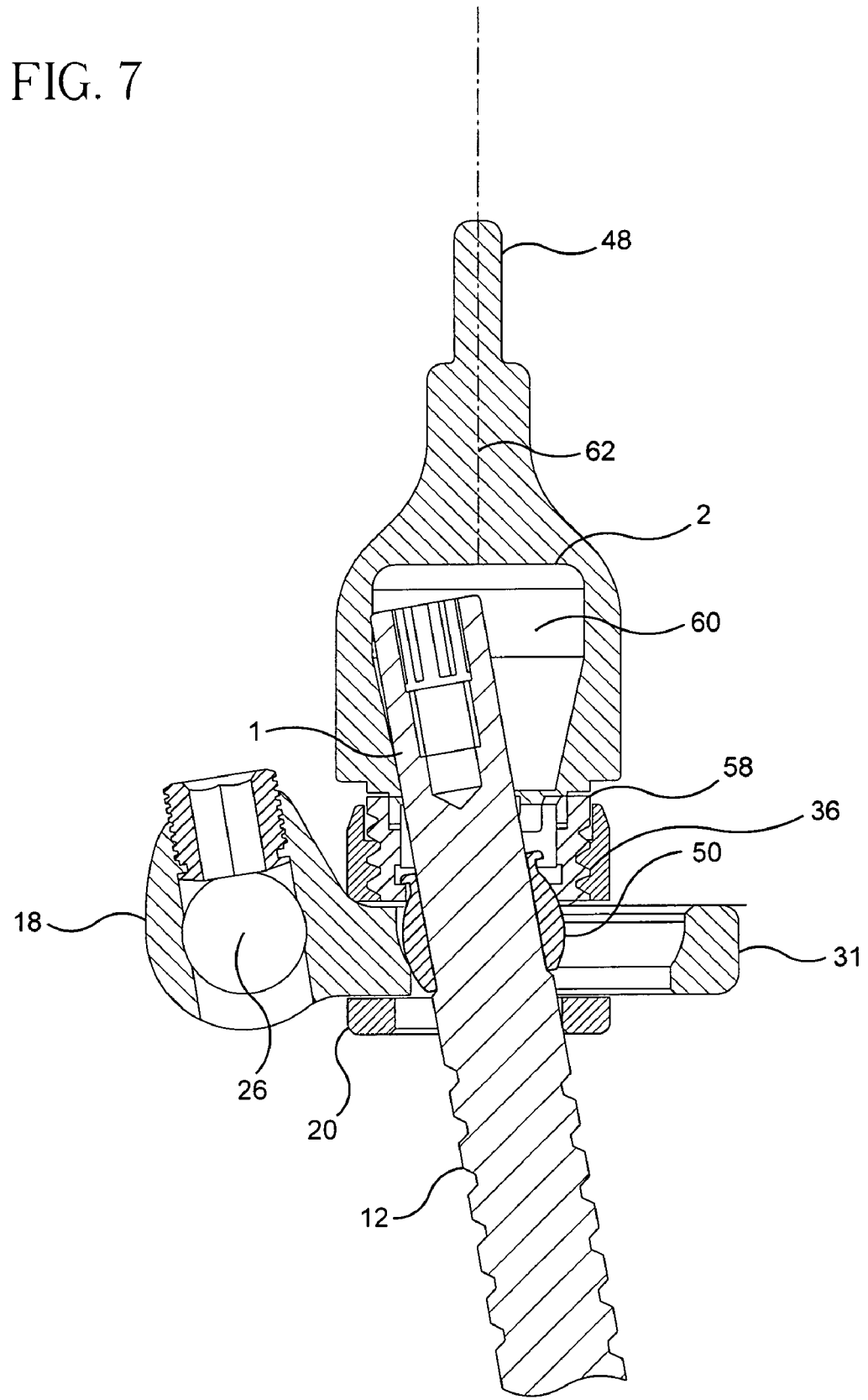
FIG. 7 is a cross-sectional view of the apparatus according to the embodiment of FIG. 1 with a tightening tool connected thereto.
Figure 8:
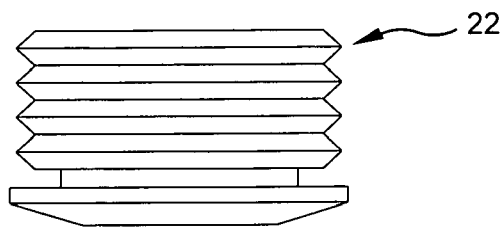
FIG. 8 is a side view of the first locking element according to the embodiment of FIG. 1.

As shown in FIG. 7, tightening instrument 48 is utilized to provide axial movement of locking nut 36. Tightening instrument 48 includes prong interface 58 for engaging the various prongs of locking nut 36, recess 60 for receiving a portion of fixation element 12, and handle 62 for the grasping and facilitation of tightening instrument 48. Upon assembly of connector 10, with fixation element 12 and spinal rod 14, at least a portion of fixation element 12 extends above sliding component 20. Typically, fixation element 12 is a polyaxial screw and the portion extending above sliding component 20 is a head generally employed for tightening fixation element 12 into the bone. Subsequent to arranging fixation element 12 in its correct axial position and sliding component 20 in its correct medial-lateral position, locking nut 36 must be tightened to prevent additional movement. Therefore, tightening instrument 48 must allow for locking nut 36 to be tightened with fixation element 12 in its correct position. Recess 60 of tightening instrument 48 provides an empty space for the acceptance of a portion of fixation element 12, typically the head portion of a polyaxial screw. In a preferred embodiment, recess 60 is large enough or configured in a manner to allow for the acceptance of the head of a polyaxial screw irregardless of its axial position. With the head of a polyaxial screw disposed within recess 60, prong interface 58 can engage prongs 46 and facilitate rotation of locking nut 36. This rotation is provided by a user grasping and rotation handle 62.

According to preferred embodiments, a variable offset connector 10 is provided with first locking element 22 and second locking element 24 pre-seated in rod receiving portion 18 and sliding component 20, respectively. In a preferred embodiment, set screw 22, locking nut 36, and ball ring 50 are all pre-seated to reduce the number of loose parts, prevent any small loose parts from being lost, and prevent any small loose parts from having to be handled and manipulated during surgery. Ball ring 50 is generally kept in the interior of locking nut 36 by the engagement of groove 53 with inner engagement surface 44. Furthermore, such elements may be permanently seated in offset connector 10, to prevent inadvertent removal therefrom. This may be accomplished through well known methods, for example, press fitting, friction locking, and the use of detents on the surfaces of the openings or elements themselves.

Another aspect of the present invention pertains to a method for performing spinal fixation. In practice, multiple connectors 10 and screws 12 are typically utilized to properly fix the vertebrae. In a preferred embodiment, at least two connectors 10 are used in conjunction with a standard spinal rod 14 and at least two polyaxial screws 12. In use, connectors 10, with or without their components pre-seated, are removed from a sterile package. Polyaxial screws 12 are then inserted into pedicles 16 of a vertebra, preferably into previously drilled pilot holes in the bone (this may be done prior to removing the connectors from their packaging). A driver or other appropriate device is used to advance the screw along its longitudinal axis into the bone. A flexible extension post (not shown) may be attached to the screws 12. This type of device aids in connecting connectors 10 with screws 12. However, it is contemplated that such a device is not required.

An appropriately sized spinal rod 14 is then chosen and bent, if needed, in accordance with the patient's anatomy. The connectors 10 are then slid over the spinal rod 14, the rod extending through first openings 26 of the connectors 10. At this point set screws 22 may be tightened, but in the alternative other devices may be used to maintain the connectors 10 on the spinal rod 14. For example, an embodiment of the present method utilizes connector clips (not shown) to maintain the connectors 10 on the spinal rod 14. These clips allow for sliding movement between connector 10 and spinal rod 14. At this point, connectors 10 may be slid onto screws 12 in pedicles 16. As discussed above, this may be more easily accomplished by utilizing flexible posts for guiding connectors 10 onto screws 12.

Connectors 10 are slid onto screws 12 until at least a portion of each screw 12 is inserted through second opening 30 and third opening 32. In a preferred embodiment, the portion of the screw 12 includes a head portion, which passes through third opening 32, elongate second opening 30, ball ring opening 54, and bore 38 of locking nut 36. Once the connectors 10 are fully slid onto screws 12, flexible posts (if utilized) are removed. The necessary spinal correction and final tightening steps are now performed. Depending upon the type of correction (i.e. —distraction or compression), such step is performed. This, in turn, moves the vertebra or vertebrae in the direction desired. The connectors are then locked onto the rod, by tightening set screws 22, as their position is determined by the movement of the respective vertebrae.

Prior to tightening locking nut 36, the axial position of screws 12 with respect to connectors 10 are adjusted by manipulating connectors 10, and thus screw 12 in tapered receiving end 40 of locking nut 36 and oppositely tapered bottom portion 33 of second opening 30. This opposite taper allows for the screw 12 to be manipulated in a broader range of angles, preferably 20 degrees polyaxially about the head portion of screw 12. Next, the medial-lateral position of screw 12 and sliding component 20 is adjusted by sliding it along extension 31 of rod receiving portion 18. After the proper axial and medial-lateral positions are determined, locking nut 36 is tightened, thereby exerting a compressive radial force on ball ring 50 and locking both the head portion of fixation element 12 and sliding component 20 in place. As discussed above, tightening instrument 48 may be used in this step.

It is contemplated that the above steps can be performed in different order. For example, set screw 22 can be tightened subsequent to the tightening of locking nut 36. Achieving sufficient angulation between anchoring elements while engaging spinal rod 14 is essential for proper spinal fixation. In a complete operation, several connectors 10 and screws 12 are utilized and connected to a single spinal rod 14. This allows for several vertebrae to be fixed. Therefore, the proper axial and medial-lateral positioning provides for a successful spinal fixation operation. Connector 10 allows a surgeon to customize such to fit different and even unique anatomy and size.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A bone fixation assembly comprising:
   a rod receiving portion having a first opening for receiving a rod, and an elongate second opening for receiving a portion of a fixation element;
   a sliding component having a third opening for receiving a portion of the fixation element, and a channel for slidably receiving a portion of said rod receiving portion, the second and third openings being alignable so that the fixation element can be inserted therethrough, the channel allowing movement of said sliding component and the fixation element with respect to said rod receiving portion and the rod disposed in said first opening;
   a first locking element associated with said rod receiving portion to secure the rod in the first opening; and
   a second locking element in direct contact with said sliding component, said rod receiving portion, and said fixation element to secure the fixation element in the second and third openings and to secure said sliding component to said rod receiving portion, said second locking element including a locking nut seated in the third opening,
   wherein tightening of the locking nut to a locked position prevents movement of said sliding component with respect to said rod receiving portion and the fixation element with respect to said sliding component and said rod receiving portion.

2. The bone fixation assembly of claim 1, wherein the second and third openings allow for the polyaxial movement of the fixation element inserted therethrough.

3. The bone fixation assembly of claim 1, further comprising a fixation element having a head portion inserted in the second and third openings.

4. The bone fixation assembly of claim 3, wherein the head portion is unthreaded.

5. The bone fixation assembly of claim 1, wherein said second locking element further comprises a ball ring that cooperates with the locking nut, the ball ring being in direct contact with said rod receiving portion and the fixation element.

6. The bone fixation assembly of claim 5, wherein the locking nut and ball ring are permanently seated in the third opening.

7. The bone fixation assembly of claim 5, wherein the locking nut includes a head having multiple prongs therein.

8. The bone fixation assembly of claim 5, wherein the locking nut contains external male threads that engage female threads formed in the third opening.

9. The bone fixation assembly of claim 8, wherein the ball ring is seated within the third opening and at least a portion of the locking nut circumferentially surrounds a portion of the ball ring.

10. The bone fixation assembly of claim 9, wherein engagement of the male threads of the locking nut with the female threads in the third opening exerts a radial force on the ball ring to secure a portion of the fixation element in the third opening.

11. The bone fixation assembly of claim 10, wherein when the locking nut is in the locked position, the ball ring is in contact with the sliding component and the locking nut, maintaining the sliding component in a fixed position.

12. The bone fixation assembly of claim 11, wherein said first locking element comprises a set screw.

13. The bone fixation assembly of claim 1, wherein the third opening has an axis substantially transverse to an axis of the first opening.

14. A variable offset connector comprising:
a rod receiving portion having a first channel adapted to receive a spinal rod and a second channel adapted to receive an unthreaded head portion of a fixation element, the fixation element being able to move in a direction towards and away from spinal rod;
a sliding component having a third channel for receiving a portion of the fixation element, and a fourth channel for slidably receiving a portion of said rod receiving portion, the second and third channels being alignable so that the unthreaded head portion of the fixation element can be inserted therethrough and the fourth channel being a closed channel;
a first locking element associated with said rod receiving portion for selectively preventing movement of the spinal rod; and
a second locking element associated with said rod receiving portion for selectively preventing movement of the fixation element, said second locking element including a locking nut seated in the third channel,
wherein tightening of the locking nut prevents movement of said sliding component with respect to said rod receiving portion and the fixation element with respect to said sliding component and said rod receiving portion.

15. The variable offset connector of claim 14, wherein the fixation element is able to move in a polyaxial direction with respect to said rod receiving portion.

16. The variable offset connector of claim 14, wherein said first channel and said second channel are substantially transverse to each other.

17. The variable offset connector of claim 14, wherein the locking nut contains external male threads that engage female threads formed in the third channel.

18. The variable offset connector of claim 17, wherein said second locking element further comprises a ball ring that cooperates with the locking nut.

19. The variable offset connector of claim 18, wherein the locking nut includes a head having multiple prongs.

20. The variable offset connector of claim 19, wherein said first locking element comprises a set screw.

21. The variable offset connector of claim 18, wherein at least a portion of the locking nut circumferentially surrounds a portion of the ball ring.

22. A bone fixation assembly comprising:
a fixation element having an unthreaded head;
a rod receiving portion having a first opening for receiving a rod, and an elongate second opening for receiving the unthreaded head;
a sliding component having a third opening for receiving a portion of the fixation element, and a channel for slidably receiving a portion of said rod receiving portion, the second and third openings being alignable so that the unthreaded head can be inserted therethrough, the channel allowing movement of said sliding component and the fixation element with respect to said rod receiving portion and the rod disposed in said first opening;
a first locking element associated with said rod receiving portion to secure the rod in the first opening;
a locking nut seated in the third opening; and
a ball ring having a ball ring portion circumferentially surrounded by said locking nut,
wherein tightening of the locking nut to a locked position prevents movement of said sliding component with respect to said rod receiving portion and the fixation element with respect to said sliding component and said rod receiving portion.

* * * * *

UNITED STATES PATENT AND TRADEMARK OFFICE
CERTIFICATE OF CORRECTION

| | |
|---|---|
| PATENT NO. | : 7,704,270 B2 |
| APPLICATION NO. | : 11/019824 |
| DATED | : April 27, 2010 |
| INVENTOR(S) | : Cédric de Coninck |

It is certified that error appears in the above-identified patent and that said Letters Patent is hereby corrected as shown below:

Column 2, line 20, "exert" should read --exerts--.
Column 4, line 45, "extension 31" should read --extension 31 and--.
Column 5, line 17, "direct with" should read --direction with--.
Column 5, line 28, "is show" should read --is shown--.
Column 5, line 63, "cause" should read --causes--.
Column 6, line 15, "Therefore, with the" should read --Therefore, the--.
Column 6, line 16, "36, prevents" should read --36 prevents--.
Column 6, line 45, "and rotation handle" should read --and rotating handle--.
Column 7, line 40, "are adjusted" should read --is adjusted--.
Column 9, line 12, Claim 14, "from spinal rod" should read --from the spinal rod--.

Signed and Sealed this
Twenty-fourth Day of July, 2012

David J. Kappos
*Director of the United States Patent and Trademark Office*